(12) United States Patent
Shioi et al.

(10) Patent No.: US 7,236,814 B2
(45) Date of Patent: Jun. 26, 2007

(54) OPTICAL MEMBER FOR BIOLOGICAL INFORMATION MEASUREMENT, BIOLOGICAL INFORMATION CALCULATION APPARATUS, BIOLOGICAL INFORMATION CALCULATION METHOD, COMPUTER-EXECUTABLE PROGRAM, AND RECORDING MEDIUM

(75) Inventors: Masahiko Shioi, Osaka (JP); Shinji Uchida, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 57 days.

(21) Appl. No.: 11/200,461

(22) Filed: Aug. 9, 2005

(65) Prior Publication Data

US 2006/0041195 A1   Feb. 23, 2006

(30) Foreign Application Priority Data

Aug. 20, 2004   (JP)   ............... 2004-241496

(51) Int. Cl.
    *A61B 5/00*   (2006.01)
(52) U.S. Cl. ...................... 600/344; 356/470
(58) Field of Classification Search ............... 600/309, 600/310, 316, 344; 356/470
    See application file for complete search history.

(56) References Cited

U.S. PATENT DOCUMENTS

| 6,128,091 | A * | 10/2000 | Uchida et al. ............. 356/432 |
| 6,445,938 | B1 | 9/2002 | Berman et al. |
| 6,584,340 | B1 | 6/2003 | Horiuchi et al. |
| 2003/0109030 | A1 | 6/2003 | Uchida et al. |
| 2004/0233433 | A1 * | 11/2004 | Uchida et al. ............. 356/364 |

FOREIGN PATENT DOCUMENTS

| EP | 1 254 631 | 11/2002 |
| JP | 09-113439 | 5/1997 |
| WO | WO 93/17621 | 9/1993 |
| WO | WO 01/47412 A1 | 7/2001 |
| WO | WO 01/58355 A1 | 8/2001 |
| WO | WO 02/38043 | 5/2002 |

OTHER PUBLICATIONS

Fukushima, et al., "Non-invasive Mensuration Technique—Development of Optical Glucose Sensor Of Blood Glucose Level" BME, Japan Society of Medical Electronics and Biological Engineering, 1991, vol. 5(8), pp. 16-21 (w/English translation).

* cited by examiner

*Primary Examiner*—Eric Winakur
*Assistant Examiner*—Etsub Berhanu
(74) *Attorney, Agent, or Firm*—RatnerPrestia

(57) ABSTRACT

An optical member for biological information measurement has a prism, which has a light incident surface being injected with emitted light, a living body tissue measuring section which a living body tissue contacts, and a light emitting surface which emits the light reflected by the living body tissue measuring section which the living body tissue contacts, or the light which has passed the living body tissue through the living body tissue measuring section which the living body tissue has contacted. A prism cover is provided so as to expose the living body tissue measuring section and to surround all or a part of the outer circumferential portion of the prism.

16 Claims, 12 Drawing Sheets

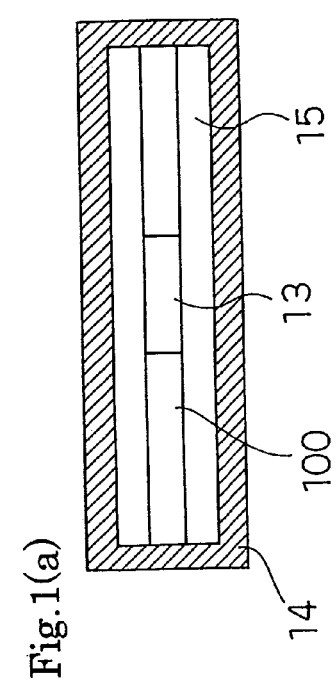
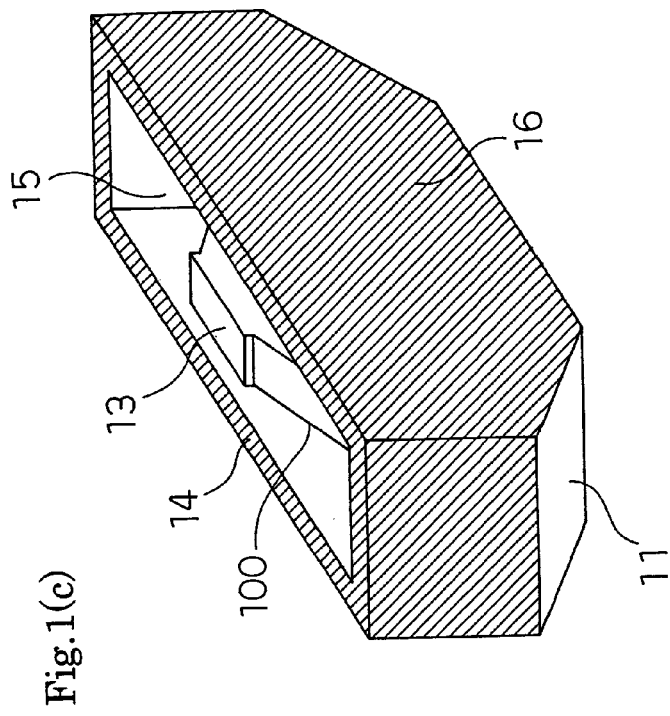
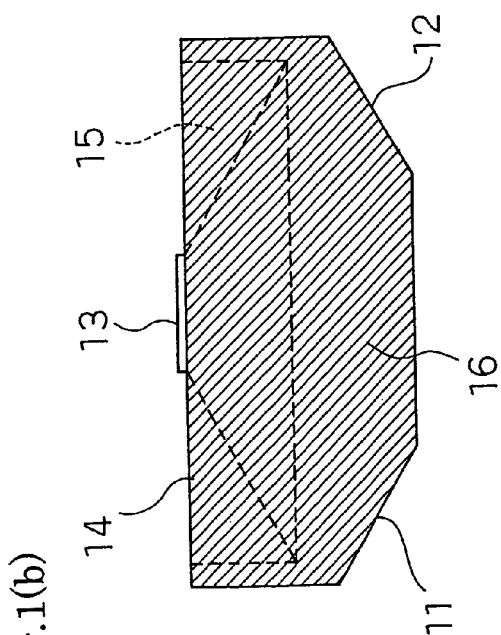
Fig.1(a)
Fig.1(b)
Fig.1(c)

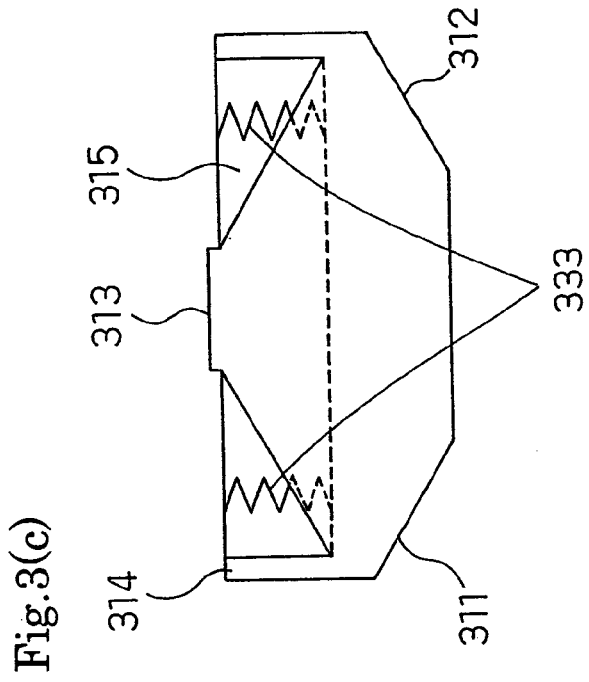
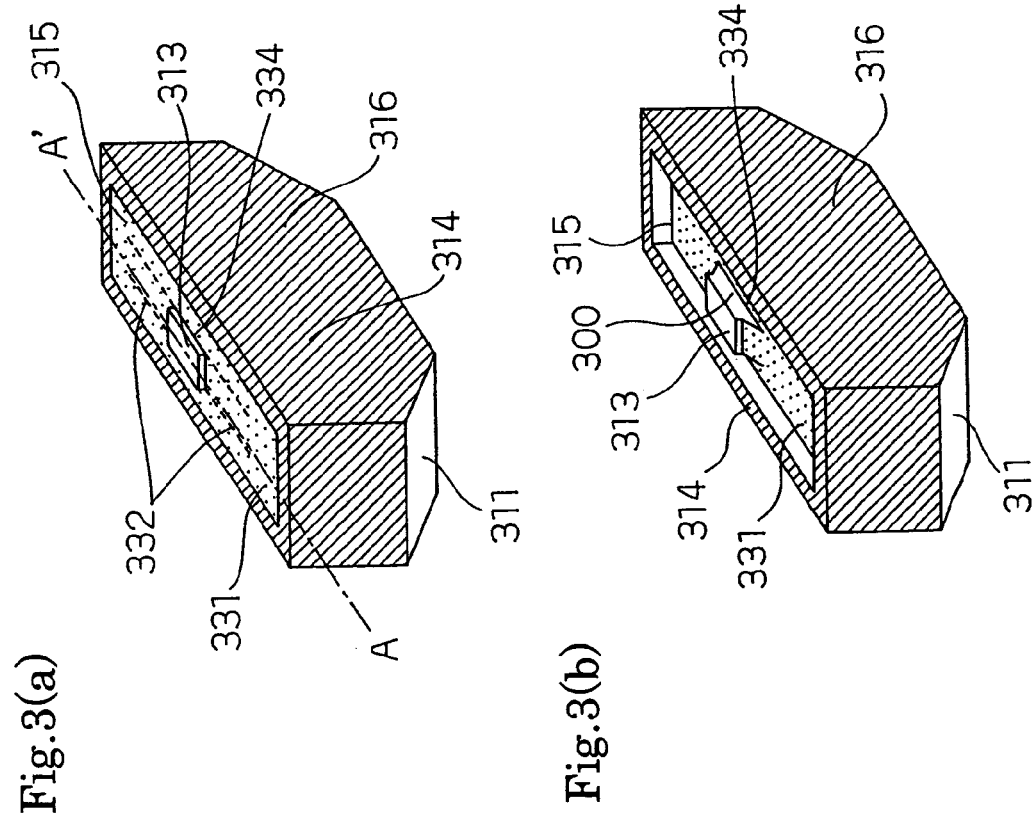
Fig.3(c)
Fig.3(a)
Fig.3(b)

OPTICAL MEMBER FOR BIOLOGICAL INFORMATION MEASUREMENT, BIOLOGICAL INFORMATION CALCULATION APPARATUS, BIOLOGICAL INFORMATION CALCULATION METHOD, COMPUTER-EXECUTABLE PROGRAM, AND RECORDING MEDIUM

BACKGROUND OF THE INVENTION

1. Field of the Invention

The present invention relates to an optical member for biological information measurement, a biological information calculation apparatus, a biological information calculation method, a computer-executable program, and a recording medium for calculating noninvasively glucose, cholesterol, urea, triglyceride, protein, and the like in body fluid by measuring a living body tissue optically.

2. Related Art of the Invention

A conventional optical measuring instrument for measuring a specific component in a living body or a solution will be described.

There exists an optical measuring instrument for measuring a blood glucose level with making upper and lower lips adhere to a transparent attenuated total reflection element having a pair of reflecting surfaces facing each other in parallel (hereafter, referred to as an ATR prism) (e.g., refer to Japanese Patent Laid-Open No. 97-113439). It is assumed that this conventional optical measuring instrument is called first conventional art.

More specifically, as shown in FIG. 12 which is a view of a conventional optical member for biological information measurement, light is injected in an ATR prism 1201 from an optical fiber 1202 in the state of holding the ATR prism 1201, which is constituted of selenium zinc, silicon, germanium or the like, in a mouth to press down the ATR prism 1201 by the lips 1203.

Then, light which repeatedly performs total reflection on boundaries between reflecting surfaces of the ATR prism 1201 and lips 1203 with infiltrating into the lips 1203 slightly (i.e., performs attenuated total reflection), and is emitted to the outside of the ATR prism 1201 is taken out and analyzes using an optical fiber 1204. Thus, it is possible to know how much the light at each wavelength is absorbed by the specific component by analyzing the light spectrum of the emitted light and calculating the amount of the light at wavelengths which the specific component which is the measuring object tends to absorb. In this way, it is possible to measure quantitatively the specific component in a living body.

In addition, there is an optical measuring instrument for measuring a blood glucose level and a blood ethanol concentration by injecting a laser beam with a wavelength of 9 to 11 μm is into this ATR prism after making the ATR prism, which is constituted of ZnSe crystal, or the like, adhere to mucosae of lips, performing multipath reflection inside the ATR prism, and analyzing attenuated total reflection light, scatter reflection light, and the like (i.e., refer to Hideo Fukushima, et al., "Non-invasive mensuration technique— development of optical glucose sensor of blood glucose level—", BME, Japan Society of Medical Electronics and Biological Engineering, 1991, vol. 5(8), p. 16-21). It is assumed that this conventional optical measuring instrument is called second conventional art.

The light which proceeds to the inside of the ATR prism is reflected after infiltrating into lips slightly.

The reflected light receives the influence of each component in body fluid which exists in lips, and decreases more than before infiltrating into lips.

Then, it is possible to obtain information on each component in the body fluid by measuring the light amount of the reflected light.

The first and a second conventional art apply an evanescent wave (being the so-called seeping light) to a quantitative analysis.

In addition, there exists a contact for biological information detection including abutting means of having a concave portion abutting against the living body tissue, detected-light emission means of emitting detected light from a part of the concave portion, and detected-light incident means which is provided in another part of the concave portion and is injected with the detected light, wherein the abutting means is constituted of a material which has a refractive index higher than a refractive index of a living body tissue, and wherein the detected light is injected into the detected-light incident means in the state that the abutting means and living body tissue abut each other after passing the living body tissue which is wrapped up in the concave portion (e.g., refer to National Publication of International Patent Application No. 2001-058355). It is assumed that this conventional contact for biological information detection is called third conventional art.

There are few damages to a living body tissue, and it is possible to measure biological information easily and highly accurately.

Nevertheless, also in the first to third conventional art, light from other than a light source for measurement such as sunlight and light from illumination may constitute disturbance light in many cases.

Thereby, the above-mentioned conventional art has a subject that an adverse effect to biological information measurement by disturbance light may arise.

In addition, in the first and second conventional art, the seeping depth d of an evanescent wave filtrating into a living body can be obtained as follows:

$$d = \frac{\lambda_0}{2\pi\sqrt{n_1^2\sin^2\theta_1 - n_2^2}} \quad \text{(Formula 1)}$$

d: Penetration depth
$\lambda_0$: Wavelength in vacuum
$n_1$: Refractive index of first medium
$n_2$: Refractive index of second medium
$\theta_1$: Incident angle from first medium to second medium With computing the case that $\lambda_0=10$ μm and $\theta_1=45°$ using ZnSe crystal ($n_1=2.0$) as the ATR prism, since a refractive index of a living body is approx 1.3 to 1.5, d becomes 29 μm at the time of $n_2=1.41$, and hence, it turns out that it is possible to obtain the information with regard to the state of approx tens of μms of surface and its vicinity.

Here, an electric field of the evanescent wave exponentially decreases according to the depth.

Hence, it is very important to make the living body tissue adhere to the living body tissue measuring section of the ATR prism.

Nevertheless, in both the first and second conventional art, the ATR prism is just held or is just pressed in lips.

Therefore, it is hard to make lips adhere to the ATR prism.

For this reason, in the first and second conventional art, the accurate measurement of biological information may become hard.

In addition, although it becomes possible in the third conventional art to upheave the living body tissue to the formed concave portion, and to measure selectively a region which is upheaved, similarly to the above-mentioned first and second conventional art, the adhesion of the living body tissue and living body tissue measuring section is very important.

Nevertheless, since the adhesion of the living body tissue and living body tissue measuring section is hard, when the adhesion of the living body tissue and living body tissue measuring section is insufficient, optical path length may vary, and the accurate measurement of biological information may become hard.

In consideration of such conventional subjects mentioned above, the present invention aims at providing an optical member for biological information measurement, a biological information calculation apparatus, a biological information calculation method, a computer-executable program, and a recording medium which can suppress the adverse effect to biological information measurement by disturbance light.

SUMMARY OF THE INVENTION

The $1^{st}$ aspect of the present invention is an optical member for biological information measurement, comprising:

an optical element having an incident surface which is injected with emitted light, a contact surface which a living body tissue contacts, and an emitting surface which emits the light that has been reflected by the contact surface in contact with the living body tissue, or the light that has passed the living body tissue via the contact surface in contact with the living body tissue; and an optical element cover provided so as to expose the contact surface and to surround all or a part of an outer circumferential portion of the optical element.

The $2^{nd}$ aspect of the present invention is the optical member for biological information measurement according to the $1^{st}$ aspect of the present invention, wherein a space, which a part of the living body tissue can enter, is formed between the optical element and the optical element cover.

The $3^{rd}$ aspect of the present invention is the optical member for biological information measurement according to the $2^{nd}$ aspect of the present invention, wherein the contact surface projects outside of the space.

The $4^{th}$ aspect of the present invention is the optical member for biological information measurement according to the $2^{nd}$ aspect of the present invention, further comprising:

a movable space cover provided so as to cover the space, wherein the space cover moves into the space when being pressed by the living body tissue in contact with the contact surface.

The $5^{th}$ aspect of the present invention is the optical member for biological information measurement according to the $4^{th}$ aspect of the present invention, wherein the space cover is held by an elastic material.

The $6^{th}$ aspect of the present invention is the optical member for biological information measurement according to the $2^{nd}$ aspect of the present invention, further comprising:

a decompressing unit of decompressing the space when the living body tissue contacts the contact surface.

The $7^{th}$ aspect of the present invention is the optical member for biological information measurement according to the $6^{th}$ aspect of the present invention, further comprising:

a movable space cover having a window provided so as to cover the space, wherein the space cover moves into the space when being pressed by the living body tissue in contact with the contact surface, and the decompressing unit decompresses the space by performing evacuation through the window.

The $8^{th}$ aspect of the present invention is the optical member for biological information measurement according to the $1^{st}$ aspect of the present invention, further comprising:

a light attenuating portion provided in all or a part of an outside of the optical element cover.

The $9^{th}$ aspect of the present invention is the optical member for biological information measurement according to the $8^{th}$ aspect of the present invention, wherein the light attenuating portion is at least one of a light reflecting element which reflects light, a light absorbing element which absorbs light, and a light scattering element which scatters light.

The $10^{th}$ aspect of the present invention is the optical member for biological information measurement according to the $1^{st}$ aspect of the present invention, wherein the contact surface has a groove.

The $11^{th}$ aspect of the present invention is the optical member for biological information measurement according to the $10^{th}$ aspect of the present invention, wherein a refractive index of the optical element is 1.55 or more.

The $12^{th}$ aspect of the present invention is the optical member for biological information measurement according to the $1^{st}$ aspect of the present invention, wherein the contact surface has a curved surface.

The $13^{th}$ aspect of the present invention is the optical member for biological information measurement according to the $1^{st}$ aspect of the present invention, wherein a portion of an end face of the optical element cover, which contacts the living body tissue, has a curved surface.

The $14^{th}$ aspect of the present invention is a biological information calculation apparatus, comprising:

the optical member for biological information measurement according to the $1^{st}$ aspect of the present invention;

a light source emitting the light;

a photodetector detecting the light emitted from the emitting surface; and an arithmetic section calculating biological information with regard to a living body, which has the living body tissue, on the basis of a result of the detection.

The $15^{th}$ aspect of the present invention is the biological information calculation apparatus according to the $14^{th}$ aspect of the present invention, wherein the biological information to be calculated is information with regard to a concentration of a material included in the living body tissue.

The $16^{th}$ aspect of the present invention is a biological information calculation method using an optical member for biological information measurement comprising an optical element having an incident surface which is injected with emitted light, a contact surface which a living body tissue contacts, and an emitting surface which emits the light that has been reflected by the contact surface in contact with the living body tissue, or the light that has passed the living body tissue via the contact surface in contact with the living body tissue, and an optical element cover provided so as to expose the contact surface and to surround all or a part of an outer circumferential portion of the optical element, comprising the steps of:

emitting the light;

detecting the light emitted from the emitting surface; and calculating biological information with regard to a living body, which has the living body tissue, on the basis of a result of the detection.

The 17th aspect of the present invention is a computer-executable program comprising computer-executable program code operable to cause a computer to execute the step of calculating biological information with regard to a living body, which has the living body tissue, on the basis of a result of the detection, in the biological information calculation method according to the 16th aspect of the present invention.

The 18th aspect of the present invention is a recording medium carrying the program according to the 17th aspect of the present invention, which can be processed by a computer.

The present invention has an advantage that it is possible to suppress the adverse effect to biological information measurement by disturbance light.

BRIEF DESCRIPTION OF THE DRAWINGS

FIG. 1(a) is a top view of an optical member for biological information measurement according to a first embodiment of the present invention, FIG. 1(b) is a side view of the optical member for biological information measurement according to the first embodiment of the present invention, and FIG. 1(c) is a perspective view of the optical member for biological information measurement according to the first embodiment of the present invention.

FIG. 3(a) is a perspective view of an optical member for biological information measurement before operation according to a second embodiment of the present invention, FIG. 3(b) is a perspective view of the optical member for biological information measurement after the operation, that is, in a state that a living body tissue is contacted to a living body tissue measuring section 313, according to the second embodiment of the present invention, and FIG. 3(c) is a sectional view, taken on line A-A', of the optical member for biological information measurement before the operation according to the second embodiment of the present invention.

DESCRIPTION OF SYMBOLS

Figure 2:
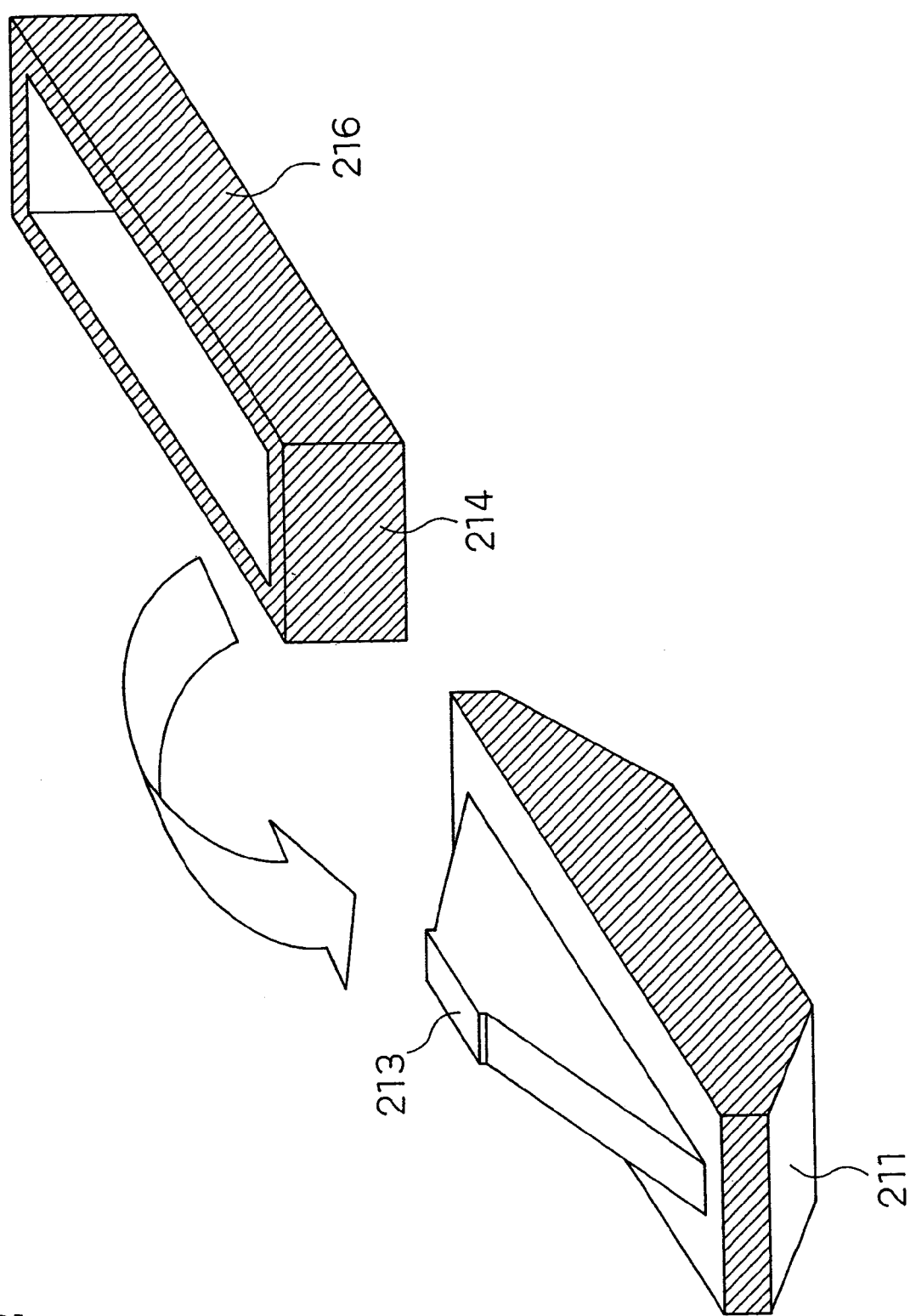
FIG. 2 is a perspective view of an optical member for biological information measurement, where a living body tissue measuring section 213 and a prism cover 214 are separated, according to an embodiment of the present invention.

11 Light Incident Surface
12 Light Emitting Surface
13 Living Body Tissue Measuring Section
14 Prism Cover
15 Living Body Tissue containing Section
16 Light Attenuating Portion
100 Prism
331 Living Body Tissue Containing Section Cover
332 Notch
333 Spring
334 Notched Portion
441 Vacuum Port
499 Pump
551 Grooves
552 Light
881 Light Source
882 Photodetector
883 Data Processing Apparatus

PREFERRED EMBODIMENTS OF THE INVENTION

Hereafter, embodiments of the present invention will be described with referring to drawings.

Embodiment 1

First, the configuration of an optical member for biological information measurement according to this embodiment will be described, mainly referring to FIGS. 1(a) to 1(c).

Here, FIG. 1(a) is a top view of the optical member for biological information measurement according to a first embodiment of the present invention, FIG. 1(b) is a side view of the optical member for biological information measurement of the first embodiment of the present invention, and FIG. 1(c) is a perspective view of the optical member for biological information measurement according to the first embodiment of the present invention.

As shown in FIG. 1(b), the optical member for biological information measurement according to this embodiment is constituted of a light incident surface 11, a light emitting surface 12, a living body tissue measuring section 13, a prism cover 14, and a living body tissue containing section 15.

That is, the optical member for biological information measurement according to this embodiment comprises a prism 100, which has a light incident surface 11 receiving emitted light, a living body tissue measuring section 13 which is a contact surface which contacts a living body tissue such as lips (not shown), and a light emitting surface 12 which emits the light reflected by the living body tissue measuring section 13 which the living body tissue contacts, and a prism cover 14 which is provided so as to expose the living body tissue measuring section 13 and to surround an outer circumferential portion of the prism 100.

It is possible to use what corresponds to a wavelength of light used for measurement as a material of the prism 100.

In addition, as specific examples of materials of the prism 100, silicon, germanium, SiC, diamond, ZnSe, ZnS, fused quartz, calcium fluoride, plastics, KrS, and the like are cited.

Here, when a material like glucose which has absorption peaks in a mid-infrared region of wave numbers of 1033 $cm^{-1}$, 1080 $cm^{-1}$, and the like and in a near-infrared region of a wavelength of 1 to 2.5 µm is measured, the material with a high transmittance in the wave number region of approx 1000 to 1100 $cm^{-1}$ in the mid-infrared region is preferable.

From such a viewpoint, it is preferable that the material of the prism 100 is silicon or germanium with small content of impurities, such as boron and phosphorus which become a cause of decrease of the above-mentioned transmittance. In addition, the resistivity of silicon or germanium becomes high as the content of impurities such as boron and phosphorus is small. For this reason, it is preferable when the resistivity is 100 Ωcm or more, and it is further preferable when the resistivity is more than 1500 Ωcm.

In the case of a near-infrared region, the material of the prism 100 is silicon or a plastic with a high refractive index. In the case of silicon, what has 100 Ωcm or more of resistivity is preferable by the same reason, and what has 1500 Ωcm or more of resistivity is further preferable. In addition, the material of the prism 100 may be calcium fluoride, fused quartz, or the like.

As shown in FIG. 1(b), the living body tissue measuring section 13 projects outside of the living body tissue containing section 15 rather than an end face of the prism cover 14 in a side where a part of the living body tissue enters.

This is for enhancing adhesion by enhancing the contact pressure of the living body tissue and living body tissue measuring section 13 by making the living body tissue measuring section 13 protrude more than the prism cover 14 although the living body tissue which is a measuring object is made to contact to the living body tissue measuring section 13 at the time of measurement.

As shown in FIG. 1(c), the prism cover 14 is provided so as to surround the living body tissue measuring section 13 as an outer circumferential portion of the optical member for biological information measurement.

Then, a light attenuating portion 16 is provided in this prism cover 14.

The light attenuating portion 16 may be something to reduce a probability that light enters into a photodetector, and hence, may be constituted of any of a light absorbing element, a light scattering element, and a light reflecting element.

An optical thin film which absorbs light at various wavelengths which is regarded as disturbance light or the like is cited as a specific example of a light absorbing element.

More specifically, it is preferable to form such an optical thin film with a monolayer or a multilayer film at suitable thickness so as to be able to absorb unnecessary light efficiently by performing multiplex interference of the light within the film.

In addition, what are cited as specific examples of the material of such an optical thin film are Cu, Cr, Mo, Fe, Ni, amorphous Si, SiC, Ge, $WSi_2$, Ti, TiN, Ta, TiW, Co, SiGe, $TiSi_2$, $CrSi_2$, $MoSi_2$, $FeSi_2$, $NiSi_2$, CrN, $MoN_2$, $SiO_2$, $Al_2O_3$, $TiO_2$, and the like.

In addition, what are cited as specific examples of the formation method of such an optical thin film are chemical vapor deposition method, a plasma vapor phase epitaxy method, a photo CVD method, a vacuum evaporation method, a liquid phase epitaxy method, a sol-gel method, an anodization reacting method, an oxidation reduction process, a laser ablation method, and the like.

What is cited as a specific example of the light scattering element or the like is the prism cover 14 whose surface is roughened by blast processing or the like so as to scatter light.

As a specific example of the light reflecting element, such as an optical thin film formed of aluminum or the like is cited.

In addition, as shown in FIG. 1(b), the living body tissue containing section 15 is provided between the living body tissue contact section 13 and prism cover 14, and is a concave portion.

In addition, the prism 100 corresponds to the optical element of the present invention, the prism cover 14 corresponds to the optical element cover of the present invention, and the light attenuating portion 16 corresponds to the light attenuating portion of the present invention.

Next, the operation of the optical member for biological information measurement according to this embodiment will be described.

First, a living body tissue is contacted to the living body tissue measuring section 13.

Then, when being further pressed, the living body tissue enters the concave portion of the living body tissue containing section 15.

In this way, by making the living body tissue enter into the living body tissue containing section 15, the adhesion of the living body tissue and living body tissue measuring section 13 is enhanced.

Since being provided in the outer circumferential portion of the living body tissue measuring section 13, the prism cover 14 forms the living body tissue containing section 15, and prevents the illumination light of a room, sunlight, radiation from a human body, and other disturbance light adversely affecting measurement from being injected into the living body tissue measuring section 13.

In addition, the example at the time of forming the optical member for biological information measurement integrally is shown. But, as shown in FIG. 2 which is a perspective view of an optical member for biological information measurement, where a living body tissue measuring section 213 and a prism cover 214 are separated, according to an embodiment of the present invention, a portion where a light attenuating portion 216 is provided in the prism cover 214 may be produced separately, and a portion which has a light incident surface 211, the living body tissue measuring section 213, and the like may be also incorporated after that. In addition, in a portion (excluding the light incident surface 211 and a light emitting surface, and being given hatching in FIG. 2) exposed to the external also after incorporation within an external surface of a portion which has the light incident surface 211, living body tissue measuring section 213, and the like, a light attenuating portion of preventing disturbance light from being injected into the living body tissue measuring section 213 may be provided.

Embodiment 2

First, the configuration of an optical member for biological information measurement according to this embodiment will be described, mainly referring to FIGS. 3(a) to 3(c).

FIG. 3(a) is a perspective view of the optical member for biological information measurement before operation according to a second embodiment of the present invention, FIG. 3(b) is a perspective view of the optical member for biological information measurement after the operation, that is, in a state that a living body tissue is contacted to a living body tissue measuring section 313, according to the second embodiment of the present invention, and FIG. 3(c) is a sectional view, taken on line A-A', of the optical member for biological information measurement before the operation according to the second embodiment of the present invention.

Although the configuration of the optical member for biological information measurement according to this embodiment is similar to the configuration of the optical member for biological information measurement according to the first embodiment mentioned above, a living body tissue containing section cover 331 is provided. In this living body tissue containing section cover 331, a notched portion 334 which has size and shape substantially equal to the living body tissue measuring section 313, and a notch 332 (shown by a dotted line in FIG. 3(a)) provided in a direction parallel to line A-A' from four corners of the notched portion 334 are provided.

Since the notched portion 334 and notch 332 are provided, the living body tissue containing section cover 331 can move with contacting the prism 300 as shown in FIG. 3(b).

From such a viewpoint, as to a material of the living body tissue containing section cover 331, it is preferable to be rubber, which has moderate elasticity, such as silicone rubber, natural rubber, or the like.

Since a spring 333 is provided as shown in FIG. 3(c), the living body tissue-containing section cover 331 moves when the living body tissue is pressed toward the living body tissue measuring section 313, and it returns to an original state when the living body tissue measuring section 313 is removed from the living body tissue.

In addition, since the provision of the spring 333 makes it possible to design a force necessary for sinking the living body tissue containing section cover 331 by appropriately selecting a spring constant of the spring 333, it is possible to perform an optimal design for the improvement of adhesion.

Furthermore, the living body tissue containing section cover 331 corresponds to the space cover of the present invention.

Next, the operation of the optical member for biological information measurement according to this embodiment will be described.

As shown in FIG. 3(a), in a prior step of contacting a living body tissue to the living body tissue measuring section 313, the living body tissue containing section 315 is shut with the living body tissue containing section cover 331.

For this reason, also when storing the optical member for biological information measurement, foreign particles such as dust do not enter into the living body tissue containing section 315 easily.

When a living body tissue is pressed by the living body tissue measuring section 313, the living body tissue containing section cover 331 sinks as shown in FIG. 3(b) by the pressure with which the living body tissue is pressed to the living body tissue measuring section 313.

Since the notched portion 334 and notch 332 as shown in FIG. 3(a) are provided in the living body tissue containing section cover 331, the living body tissue containing section cover 331 can sink as shown in FIG. 3(b).

Since the spring 333 is provided as shown in FIG. 3(c), the living body tissue containing section cover 331 sinks when a living body tissue is pressed to the living body tissue measuring section 313, and it returns to an original state when the living body tissue is removed from the living body tissue measuring section 313.

In addition, an elastic material such as rubber may be used instead of the spring 333.

Furthermore, although it is not necessary to always provide a light attenuating portion like a light attenuating portion 316, provided in the prism cover 314, in the living body tissue containing section cover 331 since it is possible to prevent radiation from the living body tissue, such a light attenuating portion may be provided.

Embodiment 3

First, the configuration of an optical member for biological information measurement according to this embodiment will be described, mainly referring to FIG. 4.

Figure 4:
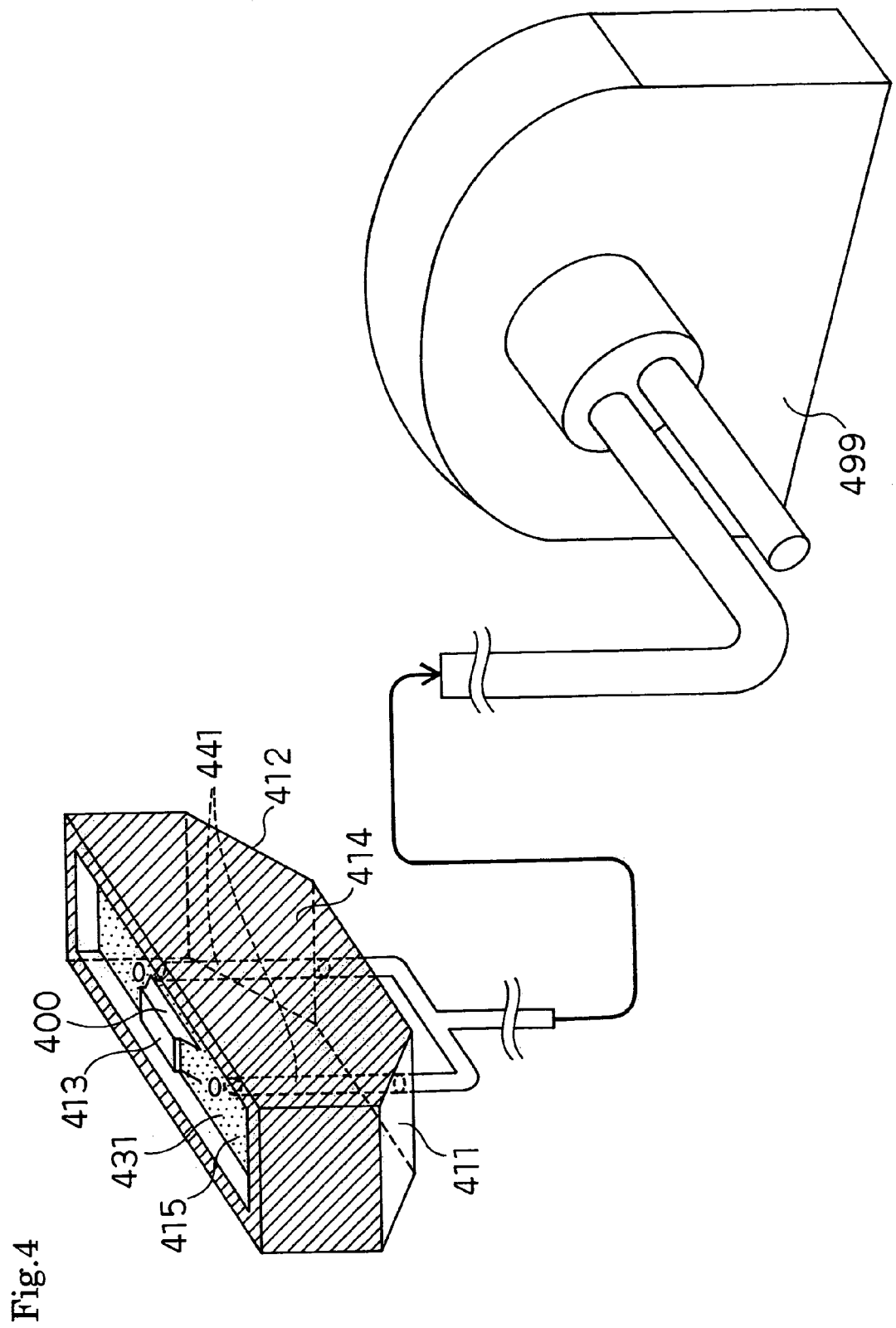
FIG. 4 is a perspective view of an optical member for biological information measurement according to a third embodiment of the present invention.

Here, FIG. 4 is a bird's eye view of the optical member for biological information measurement according to the third embodiment of the present invention.

Although the configuration of the optical member for biological information measurement according to this embodiment is similar to the configuration of the optical member for biological information measurement according to the second embodiment mentioned above, vacuum ports 441 which penetrate a prism 400 and a bottom face section of a prism cover 414 are provided.

Of course, round windows are provided also in the living body tissue containing section cover 431 in positions of overlapping with the vacuum ports 441.

Therefore, a pump 499 can decompress the interior of a living body tissue containing section 415 by performing evacuation through such windows when the living body tissue containing section cover 431 is pressed with the living body tissue in contact with the prism 400 and sinks into the interior of the living body tissue containing section 415.

In addition, the pump 499 corresponds to the decompressing unit of the present invention.

Next, the operation of the optical member for biological information measurement according to this embodiment will be described.

After contacting a living body tissue to the living body tissue measuring section 413, exhaust is performed by sucking air from the vacuum ports 441 using the pump 499.

Then, adhesion is increased by making the inside of the living body tissue containing section 415 negative pressure.

In addition, a hole for suction may be provided so as to penetrate a side face portion of the prism cover 414. Of course, in such a case, depending on a position of the hole for suction, a window does not need to be provided in the living body tissue containing section cover 431.

Figure 9:
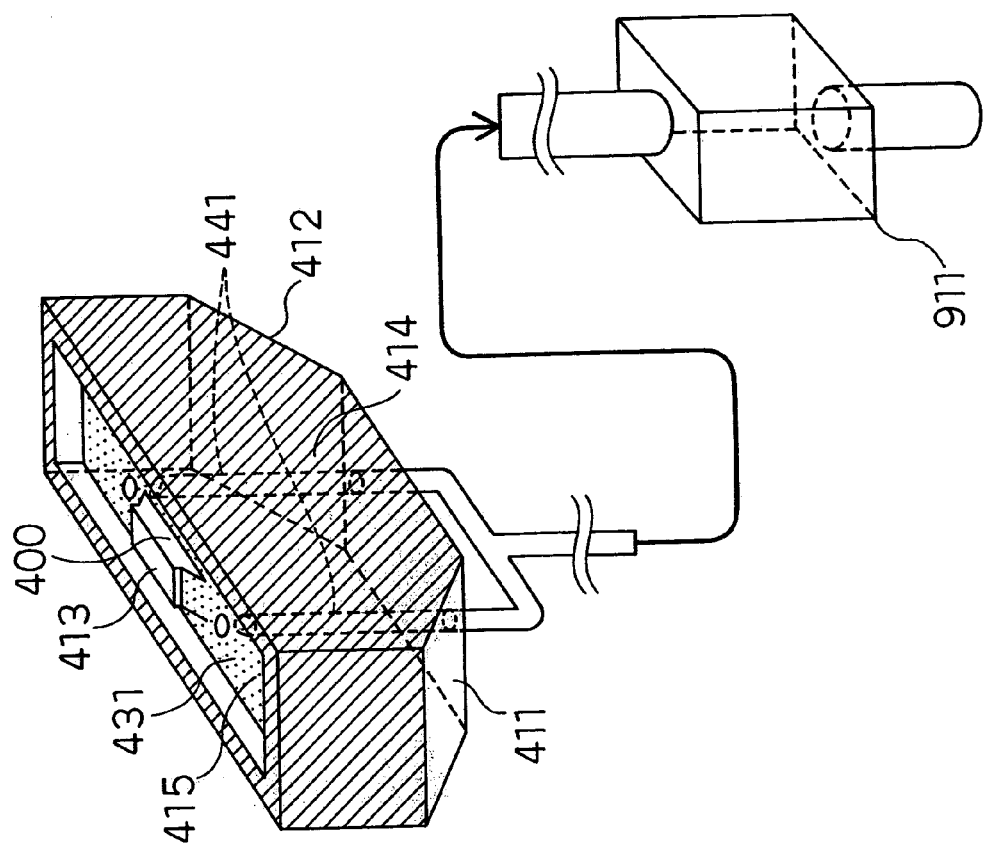
FIG. 9 is a perspective view of an optical member for biological information measurement, where a one-way valve 911 is provided in a vacuum port 441, according to an embodiment of the present invention.

In addition, although the example using the pump 499 is shown, as shown in FIG. 9 which is a bird's eye view of the optical member for biological information measurement in which a one-way valve 911 is provided in the vacuum ports 441, which is an embodiment of the present invention, the one-way valve 911 which has a check valve may be provided in the vacuum ports 441. More specifically, what may be used is such configuration of a sucker that, when a living body tissue fulfills the living body tissue containing section 415 when the living body tissue is pressed by the living body tissue measuring section 413, air in the living body tissue containing section 415 is evacuated through the one-way valve 911 from the vacuum ports 441 and the living body tissue adheres to the living body tissue measuring section 413.

The first to third embodiments are described above in detail.

Figure 5A:
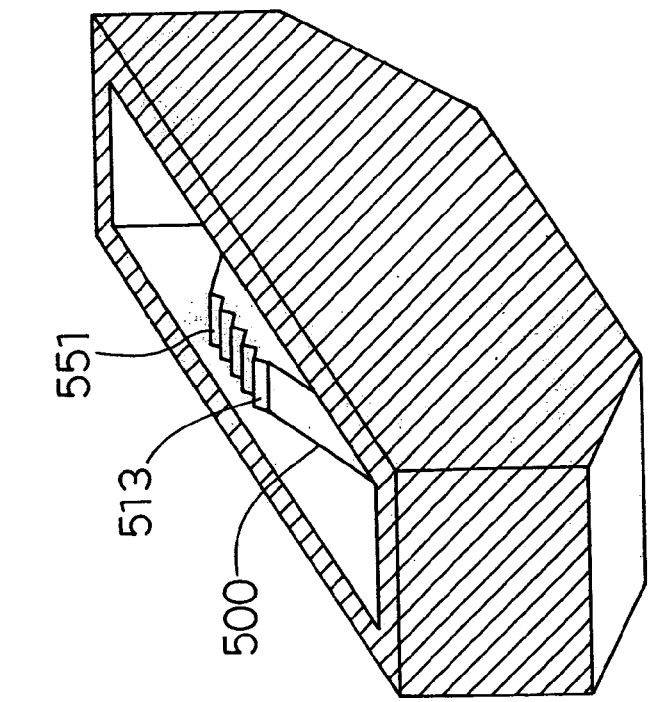
FIG. 5(a) is a perspective view of an optical member for biological information measurement, where a living body tissue measuring section 513 has grooves 551, according to an embodiment of the present invention.
Figure 5B:
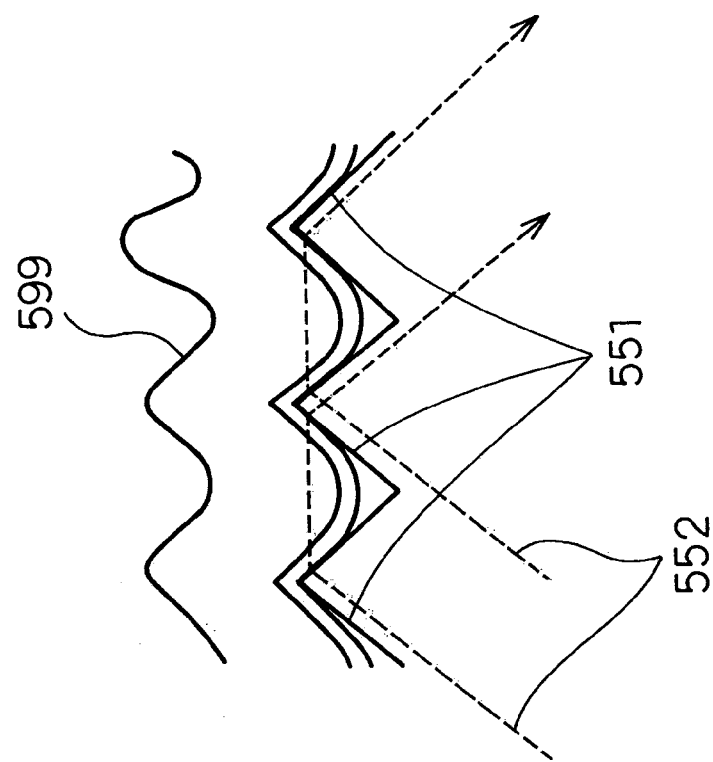
FIG. 5(b) is a schematic diagram of the grooves 551 according to an embodiment of the present invention, at the time when a living body tissue 599 adheres thereto and light 552 is transmitting the inside of the living body tissue 599 adhered.

(A) In addition, although the case that a living body tissue measuring section is nearly planate is described, what may be used is a prism 500 where a living body tissue measuring section 513 has grooves 551, as shown in FIG. 5(*a*) which is a perspective view of the optical member for biological information measurement, where the living body tissue measuring section 513 has grooves 551, according to the embodiment of the present invention, and FIG. 5(*b*) which is a schematic diagram at the time when a living body tissue 599 adheres the grooves 551 and light 552 is transmitting the inside of the living body tissue 599 adhered, according to the embodiment of the present invention.

As shown in FIG. 5(*b*), measurement is performed by making the living body tissue 599 adhere to a plurality of grooves 551, which are provided in the living body tissue measuring section 513, and making light 552 transmit the living body tissue 599.

Thereby, the optical path length of the light 552 having passed the living body tissue 599 through the living body tissue measuring section 513 which the living body tissue 599 has contacted is determined by a dimension of one groove of the plurality of grooves 551. Hence, as apparent from the Lambert Beer's law shown in the following formula, the optical path length is determined mechanically by a dimension of the grooves 551, and hence, it is possible to perform measurement with sufficient accuracy:

$$A = \sum_i \varepsilon_i C_i l \quad \text{(Formula 2)}$$

A: Absorbance
i: Component number
$\varepsilon_i$: Molar absorption coefficient of i-th component
$C_i$: Concentration of i-th component
l: Optical path length for transmitting medium In order that the light 552, which was emitted from a surface of a groove of the plurality of grooves 551, is refracted at an interface between the surface and the living body tissue 599, goes straight through the living body tissue 599 as far as an interface between the other surface of the groove and the living body tissue 599, and is again refracted at the interface to come back to the other surface (refer to FIG. 5(*b*)), it is preferable that a refractive index of the prism 500 is 1.55 or more which is higher than a living body's refractive index of 1.3 to 1.5.

Figure 10A:
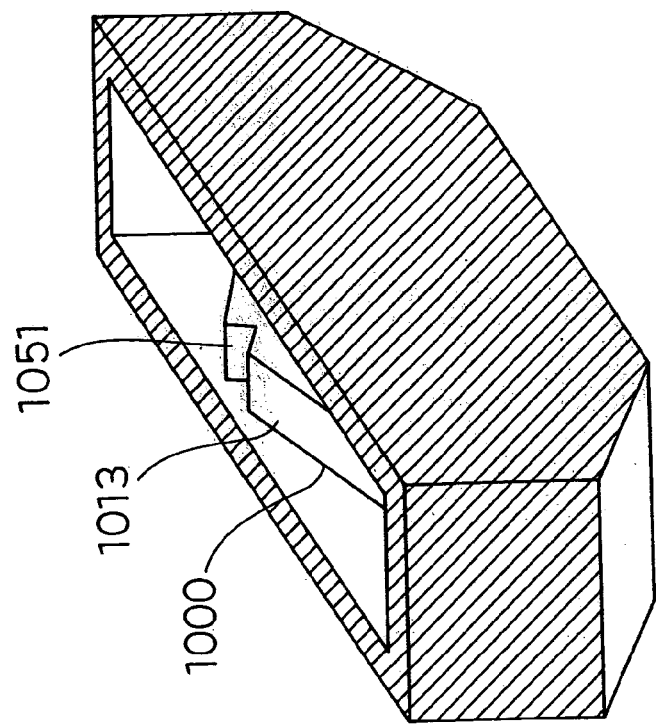
FIG. 10(a) is a perspective view of an optical member for biological information measurement, where a living body tissue measuring section 1013 has a groove 1051, according to an embodiment of the present invention.
Figure 10B:
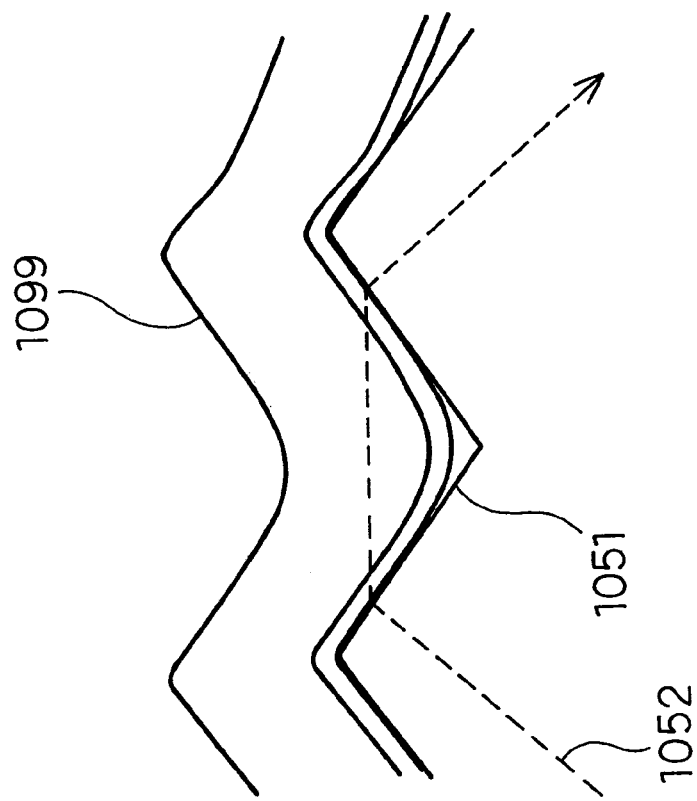
FIG. 10(b) is a schematic diagram of an embodiment of the present invention, at the time when a living body tissue 1099 adheres to the groove 1051 and light 1052 is transmitting the inside of the living body tissue 1099 adhered.

Of course, although the case that the plurality of grooves 551 are provided is described, it is also good to use a prism 1000 where a living body tissue measuring section 1013 has one groove 1051, as shown in FIG. 10(*a*) which is a perspective view of an optical member for biological information measurement, where the living body tissue measuring section 1013 has the groove 1051, according to an embodiment of the present invention, and FIG. 10(*b*) which is a schematic diagram according to an embodiment of the present invention at the time when a living body tissue 1099 adheres to the groove 1051 and light 1052 is transmitting the inside of the living body tissue 1099 adhered.

Figure 6:
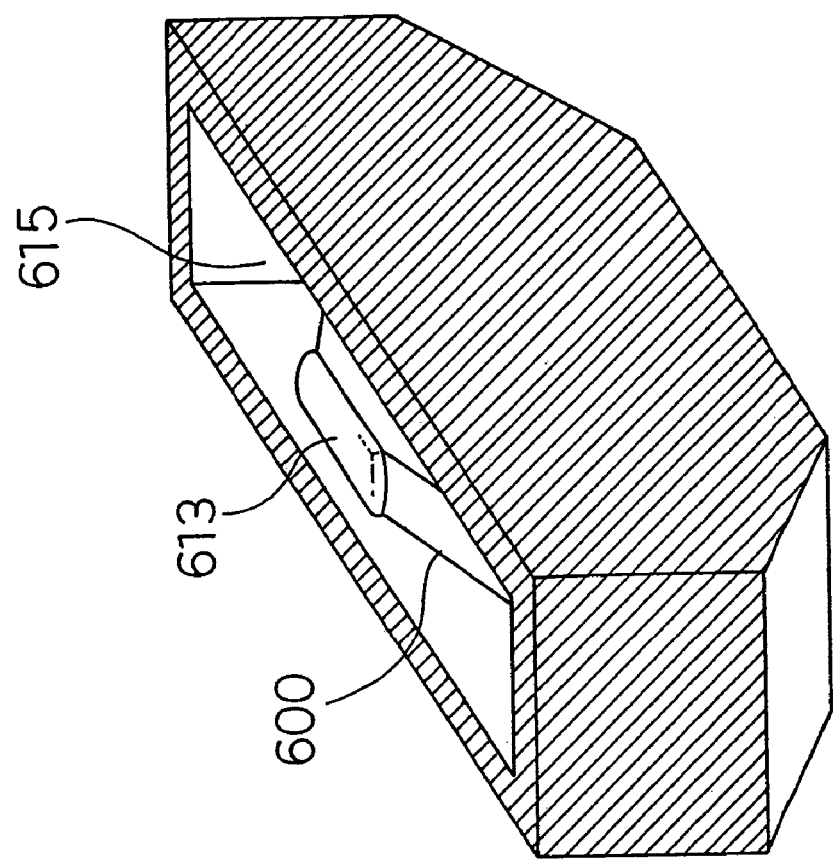
FIG. 6 is a perspective view of an optical member for biological information measurement, which has a living body tissue measuring section 613 with a round portion contacting to a living body tissue, according to an embodiment of the present invention.

(B) In addition, as shown in FIG. 6 which is a perspective view of an optical member for biological information measurement, which has a living body tissue measuring section 613 with a round portion contacting to a living body tissue, according to an embodiment of the present invention, it is also good to make an outer circumferential portion of the living body tissue measuring section 613 a curved surface.

Thereby, it is possible to reduce a pain when pushing a living body tissue against the living body tissue measuring section 613 of the prism 600.

Furthermore, since the curved surface of the outer circumferential portion of the living body tissue measuring section 613 is roundish in any direction, it is possible to reduce the pain securely.

Moreover, since it becomes easy for a living body tissue to be introduced into the living body tissue containing section 615 and the deformation of the living body tissue becomes further gentle in comparison with the case that the outer circumferential portion of the living body tissue measuring section 613 is not a curved surface, it is possible to increase the adhesion of the living body tissue and living body tissue measuring section 613.

Of course, it is also good to provide grooves like the grooves 551 in the living body tissue measuring section 613 while making the outer circumferential portion of the living body tissue measuring section 613 a curved surface.

Figure 7:
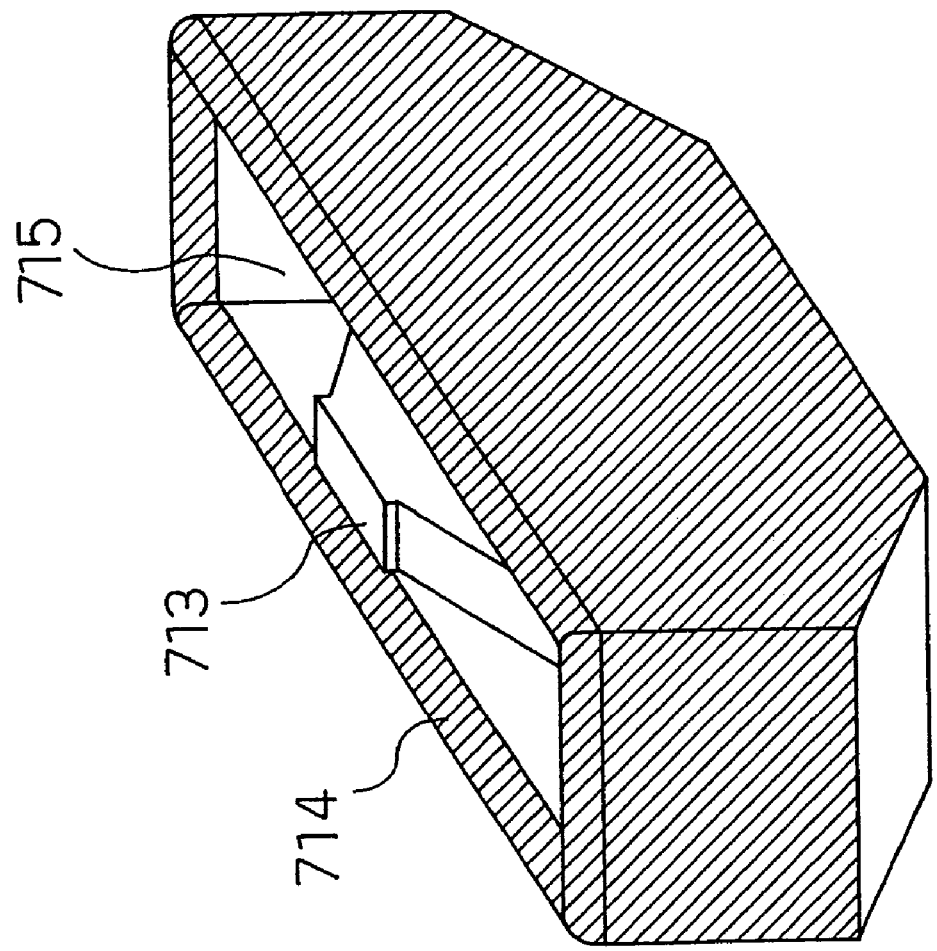
FIG. 7 is a perspective view of an optical member for biological information measurement, which has a prism cover 714 with a round portion contacting to a living body tissue, according to an embodiment of the present invention.

(C) In addition, it is also good to make a portion of an end face of a prism cover 714 in contact with a living body tissue a curved surface, as shown in FIG. 7 which is a bird's eye view of the optical member for biological information measurement having the prism cover 714 whose portion in contact with the living body tissue is round, according to an embodiment of the present invention.

Doing this is preferable since it is possible to reduce a pain when a living body tissue is pressed against the living body tissue measuring section 713 and it becomes easy for the living body tissue to be introduced by the living body tissue containing section 715.

Figure 11B:
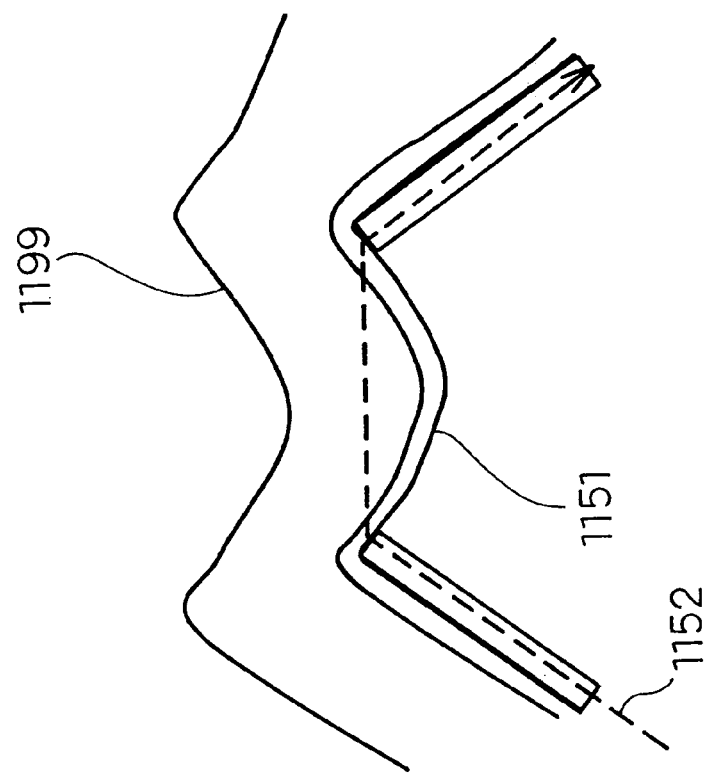
FIG. 11(b) is a schematic diagram of an embodiment of the present invention, at the time when a living body tissue 1199 adheres to a gap 1151 and light 1152 is transmitting the inside of the living body tissue 1199 adhered.
Figure 11A:
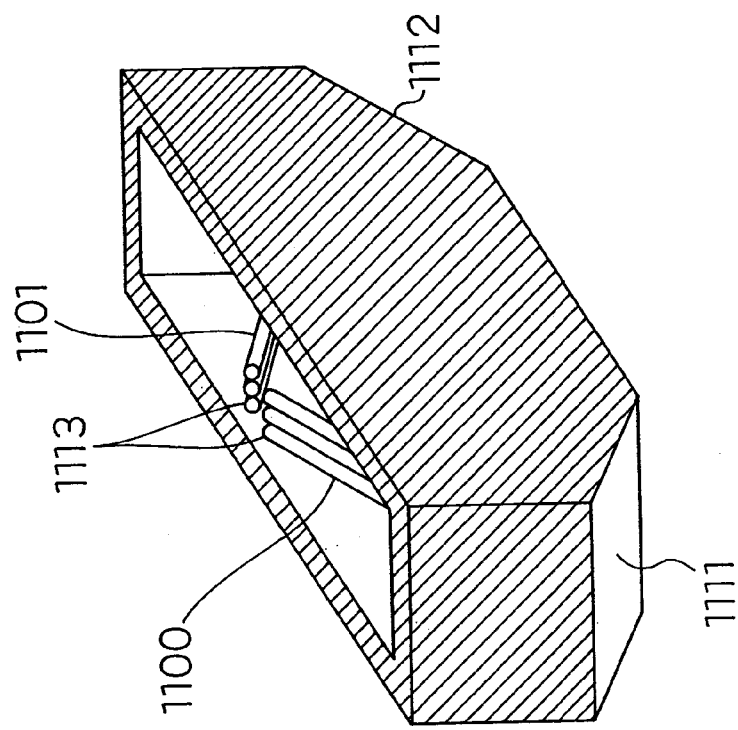
FIG. 11(a) is a perspective view of an optical member for biological information measurement, which has optical fiber bundles 1100 and 1101 having living body tissue measuring sections 1113 as end portions of the optical fiber, according to an embodiment of the present invention.
Figure 12:
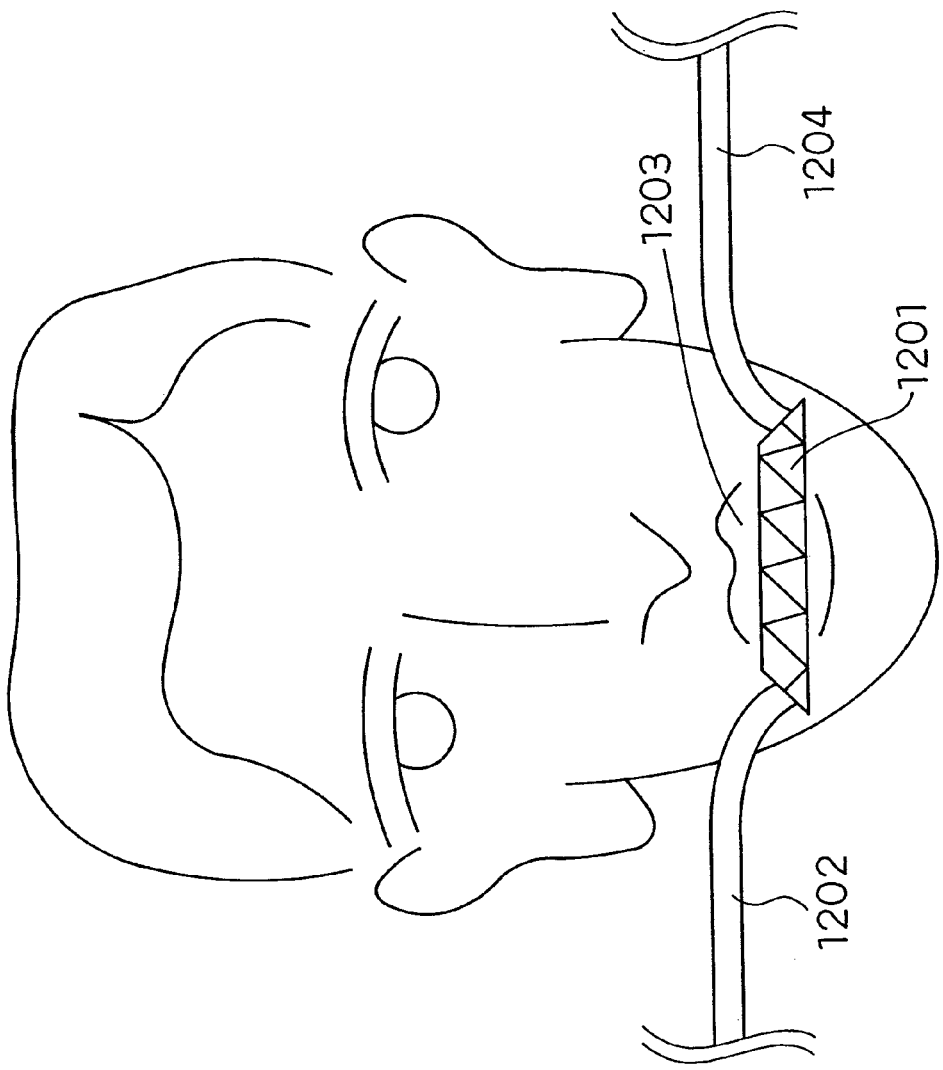
FIG. 12 is a view of a conventional optical member for biological information measurement.

(D) In addition, although the case that a prism is used is described, it is also good to use optical fiber bundles 1100 and 1101 as shown in FIG. 11(*a*) which is a bird's eye view of an optical member for biological information measurement, which has the optical fiber bundles 1100 and 1101 having living body tissue measuring sections 1113 as end portions, according to an embodiment of the present invention, and FIG. 11(*b*) which is a schematic diagram of an embodiment of the present invention, at the time when a living body tissue 1199 adheres to a gap 1151 and light 1152 is transmitting the inside of the living body tissue 1199 adhered.

The light 1152 enters into the optical fiber bundle 1100 from a light incident surface 1111, passes the optical fiber bundle 1100 and enters into the living body tissue 1199 from an end portion of the optical fiber in a side of the gap 1151. Then, the light 1152 is emitted from the living body tissue 1199, enters into the optical fiber bundle 1101 from an end portion of the optical fiber in a side of the gap 1151 of the optical fiber bundles 1101, passes the optical fiber bundle 1101, and is emitted from a light emitting surface 1112.

Doing this is preferable since the weight saving of the optical member for the biological information measurement is realizable.

Embodiment 4

First, the configuration of a biological information calculation apparatus according to this embodiment will be described, mainly referring to FIG. 8.

Figure 8:
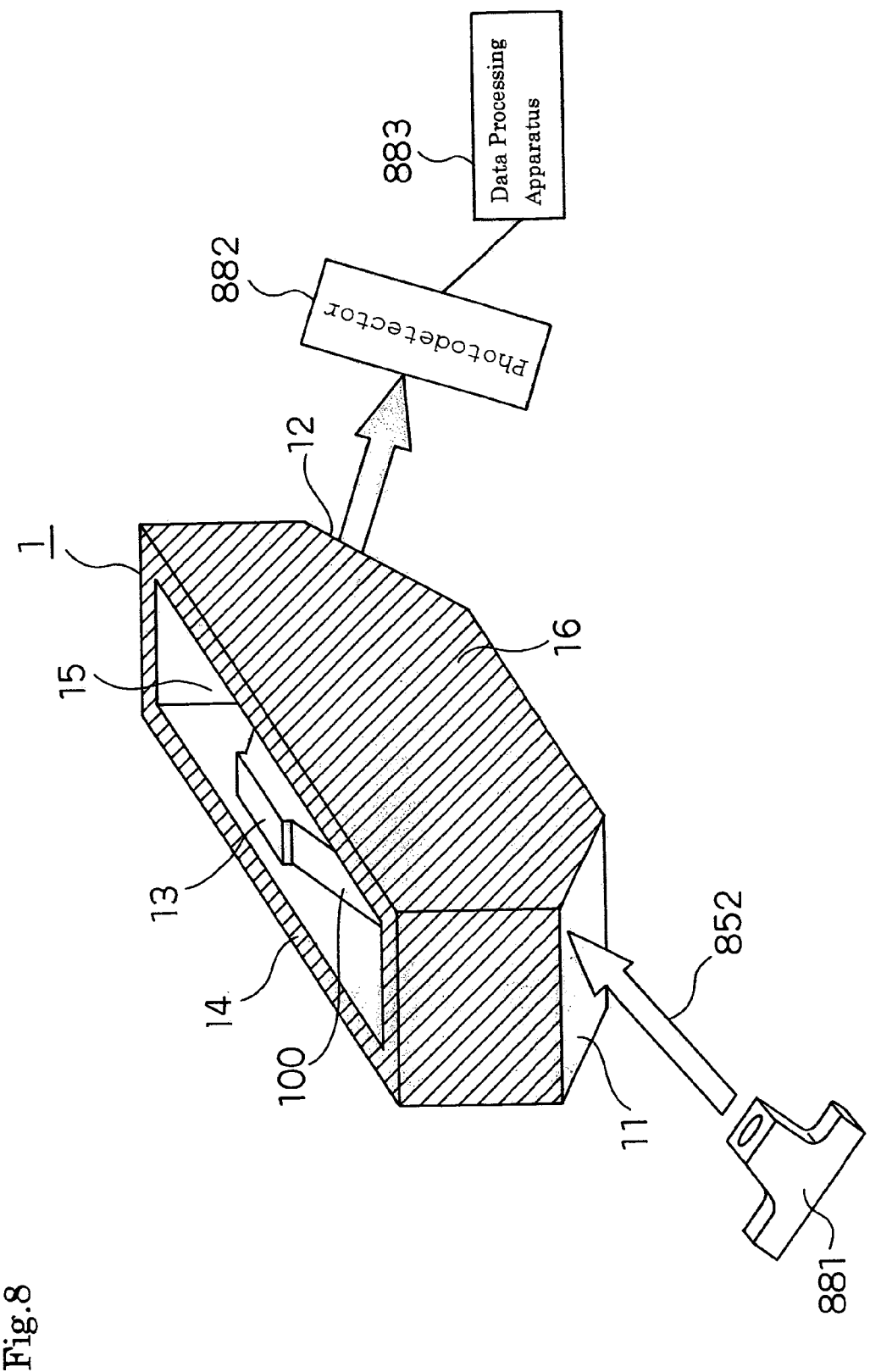
FIG. 8 is a schematic diagram of a biological information calculation apparatus according to a fourth embodiment of the present invention.

Here, FIG. 8 is a schematic diagram of the biological information calculation apparatus according to a fourth embodiment of the present invention.

The biological information calculation apparatus of this embodiment is constituted of a light source 881 which emits light, the optical member 1 for biological information measurement described in the first embodiment mentioned above, a photodetector 882 which detects the light emitted from the prism 100, and a data processing apparatus 883 which calculates biological information with regard to a living body, which has a living body tissue, on the basis of a result of the detection.

Of course, it is also good to provide a spectroscope (not shown), such as a spectroscopic instrument using a grating, a Fourier transform spectroscopic instrument, or the like, between the light source 881 and optical member 1 for biological information measurement.

The light source 881 is means of emitting light at an absorption wavelength of a measurement component which is a measuring object, such as an LD, an LED, a halogen light source, a semiconductor laser, a Glover light source formed by sintering SiC cylindrically, a $CO_2$ laser, a tungsten lamp, or the like. In addition, the case that the light source 881 is an LD is shown.

Here, when a material like glucose which has absorption peaks in a mid-infrared region of wave numbers of 1033 $cm^{-1}$, 1080 $cm^{-1}$, and the like and in a near-infrared region of a wavelength of 1- to 2.5 μm is measured, the Glover light source is preferable from the viewpoint of being able to cover a comparatively wide wave range and emitting light favorably also in a long wavelength region which is about 10 μm, when measuring infra-red light. In addition, when measuring 1000 to 2500 nm near-infrared light, the halogen light source is preferable as the light source 881.

In this way, it is desirable to include the light which has a wavelength between 1000 nm and 10000 nm as the emitted light.

The photodetector 882 is means of an MCT detector using mixed crystal of mercury, tellurium and cadmium, a pyroelectric sensor, a DTGS detector, a thermistor, a thermopile, a Golay cell, or the like in the case of amid-infrared region, and a PbS detector, an InSb detector, a PbSe detector, an InGaAs detector, a Si detector, or the like in the case of a near-infrared region.

The data processing apparatus 883 is a computer.

What is cited as a specific example of biological information to be calculated is information or the like with regard to a concentration of glucose, triglyceride, urea, cholesterol (total cholesterol), protein, or the like.

In addition, the light source 881 corresponds to the light source of the present invention, the photodetector 882 corresponds to the photodetector of the present invention, and the data processing apparatus 883 corresponds to the arithmetic section of the present invention.

Next, the operation of the biological information calculation apparatus according to this embodiment will be described.

In addition, one embodiment of the biological information calculation method of the present invention will be also described, with describing the operation of the biological information calculation apparatus of this embodiment.

Light 852 emitted from the light source 881 enters into the optical member 1 for biological information measurement.

The light 852 entering into the optical member 1 for biological information measurement is transmitted, scattered, and absorbed with a living body tissue in contact with the living body tissue measuring section 13, and is emitted from the light emitting surface 12 of the optical member 1 for biological information measurement.

The light 852 emitted from the optical member 1 for biological information measurement is detected by the photodetector 882.

The data processing apparatus 883 calculates biological information using the result of detection by the photodetector 882.

According to this embodiment, since the optical member 1 for biological information measurement described in the first embodiment mentioned above is used, it is possible to reduce the influence of stray light which enters from faces other than a living body tissue measuring section, to increase the adhesion of a living body tissue and an optical element, and to calculate the concentration of a target component in a device under test stably and easily, and hence, this is useful for measurement of, for example, a body fluid component in a medical application.

In addition, the program of the present invention is a program for making a computer execute the operation of all or a part of steps of the biological information calculation method of the present invention mentioned above, and is a program which operates with collaborating with a computer.

Furthermore, the recording medium of the present invention is a recording medium which holds a program for executing the operation of all or a part of steps of the biological information calculation method of the present invention mentioned above by a computer, the program which can be read by a computer and executes the above-mentioned operation with collaborating with the above-mentioned computer.

Moreover, the above-mentioned "a part of steps" of the present invention means one or some steps of a plurality of those steps.

In addition, the above-mentioned "operation of a step" of the present invention means the operation of all or a part of the above-mentioned step.

Furthermore, one utilizing form of the program of the present invention may be an aspect of being recorded in a recording medium which a computer can read, and operating with collaborating with the computer.

Moreover, another utilizing form of the program of the present invention may be an aspect which is transmitted inside a transmission medium, is read by a computer, and operates with collaborating with the computer.

In addition, as recording media, ROM and the like are included, and as transmission media, transmission media such as the Internet, light, electric waves, acoustic waves, and the like are included.

Furthermore, the computer of the present invention mentioned above may be not only pure hardware such as a CPU, but also firmware, OS, and further, what includes a peripheral device.

In addition, as described above, the configuration of the present invention may be achieved in software or hardware.

An optical member for biological information measurement, a biological information calculation apparatus, a biological information calculation method, a computer-executable program, and a recording medium according to the present invention can suppress an adverse effect to biological information measurement by disturbance light, and hence, are useful.

What is claimed is:

1. An optical member for biological information measurement, comprising:
    an optical element having an incident surface which receives emitted light, a contact surface configured to be in contact with a living body tissue, and an emitting surface which emits the light that has been reflected by the contact surface in contact with the living body tissue, or the light that has passed the living body tissue via the contact surface in contact with the living body tissue; and
    an optical element cover provided so as to expose the contact surface and to surround a side surface of the optical element, wherein the side surface of the optical element is configured adjacent to the contact surface, and said optical element cover is positioned so as to form a space between the side surface and the optical element cover within which a part of the living body tissue can enter when the living body tissue contacts the contact surface.

2. The optical member for biological information measurement according to claim 1, wherein the contact surface projects outside of the space.

3. The optical member for biological information measurement according to claim 1, further comprising:
    a movable space cover provided so as to cover the space, wherein the space cover moves into the space when being pressed by the living body tissue in contact with the contact surface.

4. The optical member for biological information measurement according to claim 3, wherein the space cover is held by an elastic material.

5. The optical member for biological information measurement according to claim 1, further comprising:
    a decompressing unit for decompressing the space when the living body tissue contacts the contact surface.

6. The optical member for biological information measurement according to claim 5, further comprising:
    a movable space cover having a window provided so as to cover the space,
    wherein the space cover moves into the space when being pressed by the living body tissue in contact with the contact surface, and
    the decompressing unit decompresses the space by performing evacuation through the window.

7. The optical member for biological information measurement according to claim 1, further comprising:
    a light attenuating portion provided in all or a part of an outside of the optical element cover.

8. The optical member for biological information measurement according to claim 7, wherein the light attenuating portion is at least one of a light reflecting element which reflects light, a light absorbing element which absorbs light, and a light scattering element which scatters light.

9. The optical member for biological information measurement according to claim 1, wherein the contact surface has a groove.

10. The optical member for biological information measurement according to claim 9, wherein a refractive index of the optical element is 1.55 or more.

11. The optical member for biological information measurement according to claim 1, wherein the contact surface has a curved surface.

12. The optical member for biological information measurement according to claim 1, wherein a portion of an end face of the optical element cover, configured to be in contacts with the living body tissue, has a curved surface.

13. A biological information calculation apparatus, comprising:
    the optical member for biological information measurement according to claim 1;
    a light source emitting light;
    a photodetector detecting the light emitted from the emitting surface; and
    an arithmetic section calculating biological information with regard to a living body, which has the living body tissue, on the basis of a result of the detection.

14. The biological information calculation apparatus according to claim 13, wherein the biological information to be calculated is information with regard to a concentration of a material included in the living body tissue.

15. A biological information calculation method using an optical member for biological information measurement comprising an optical element having an incident surface which receives emitted light, a contact surface which a living body tissue contacts, and an emitting surface which emits the light that has been reflected by the contact surface in contact with the living body tissue, or the light that has passed the living body tissue via the contact surface in contact with the living body tissue, and an optical element cover provided so as to expose the contact surface and to surround a side surface of the optical element, wherein the side surface of the optical element is configured adjacent to the contact surface, and said optical element cover is positioned so as to form a space between the side surface and the optical element cover within which a part of the living body tissue can enter when the living body tissue contacts the contact surface, comprising the steps of:
    emitting light;
    detecting the light emitted from the emitting surface;
    calculating biological information with regard to a living body, which ahs the living body tissue, on the basis of a result of the detection; and
    displaying the calculated biological information.

16. The method for biological information calculation according to claim 15, wherein the contact surface projects outside of the space.

* * * * *

UNITED STATES PATENT AND TRADEMARK OFFICE
CERTIFICATE OF CORRECTION

PATENT NO. : 7,236,814 B2  Page 1 of 1
APPLICATION NO. : 11/200461
DATED : June 26, 2007
INVENTOR(S) : Masahiko Shioi et al.

It is certified that error appears in the above-identified patent and that said Letters Patent is hereby corrected as shown below:

Title Page, Item (56) References Cited, FOREIGN PATENT DOCUMENTS
change "WO    WO 93/17621  9/1993"
to -- WO    93/17621    9/1993 --

Title Page, Item (56) References Cited, FOREIGN PATENT DOCUMENTS
change "WO    WO 01/47412 A1    7/2001"
to -- WO    01/47412 A1    7/2001 --

Title Page, Item (56) References Cited, FOREIGN PATENT DOCUMENTS
change "WO    WO 01/58355 A1    8/2001"
to -- WO    01/58355 A1    8/2001 --

Title Page, Item (56) References Cited, FOREIGN PATENT DOCUMENTS
change "WO    WO 02/38043    5/2002"
to -- WO    02/38043    5/2002 --

Column 16
Line 16, change "contacts" to -- contact --

Signed and Sealed this

Eighteenth Day of December, 2007

JON W. DUDAS
*Director of the United States Patent and Trademark Office*